United States Patent [19]

Schuster et al.

[11] Patent Number: 5,210,335

[45] Date of Patent: May 11, 1993

[54] PREPARATION OF LOWER POLYHYDRIC ALCOHOLS

[75] Inventors: Ludwig Schuster, Limburgerhof; Walter Himmele, Walldorf, both of Fed. Rep. of Germany

[73] Assignee: BASF Aktiengesellschaft, Ludwigshafen, Fed. Rep. of Germany

[21] Appl. No.: 912,034

[22] Filed: Jul. 9, 1992

Related U.S. Application Data

[63] Continuation of Ser. No. 785,223, Oct. 28, 1991, abandoned, which is a continuation of Ser. No. 555,663, Jul. 18, 1990, abandoned, which is a continuation of Ser. No. 385,545, May 26, 1989, abandoned.

[30] Foreign Application Priority Data

May 28, 1988 [DE] Fed. Rep. of Germany .... 3818198.3

[51] Int. Cl.$^5$ ...................... C07C 29/132; C07C 31/20
[52] U.S. Cl. ..................................... 568/863; 568/861; 568/903
[58] Field of Search ......................................... 568/863

[56] References Cited

U.S. PATENT DOCUMENTS

| | | | |
|---|---|---|---|
| 1,915,431 | 6/1933 | Lautenschlager et al. | 568/863 |
| 1,990,245 | 2/1935 | Mueller et al. | 568/863 |
| 2,325,206 | 7/1943 | Stengel | 568/863 |
| 2,518,235 | 8/1950 | Hartstra et al. | 568/863 |
| 2,549,416 | 4/1951 | Brooks | 568/881 |
| 2,759,023 | 8/1956 | Kool et al. | 568/863 |
| 4,029,878 | 6/1977 | Kruse | 568/863 |
| 4,380,679 | 4/1983 | Arena | 568/863 |
| 4,382,150 | 5/1983 | Arena | 568/863 |
| 4,401,823 | 8/1983 | Arena | 568/863 |
| 5,004,845 | 4/1991 | Bradley et al. | 568/885 |

OTHER PUBLICATIONS

Handbook of Chemistry & Physics, 32nd ed. (1950) pp. 1521 and 1522.
G. V. Ling et al, Ind. Eng. Chem. Prod. Res. Develop., vol. 9, No. 2, 1970, pp. 210–212.
G. Natta et al, Chem. Berichte 76 7 (1943) Table 1, pp. 641–657.
R. Weidenhagen and H. Wegner, Chem. Ber. 71, 12 (1938), pp. 2712–2716.

*Primary Examiner*—Joseph E. Evans
*Attorney, Agent, or Firm*—John H. Shurtleff

[57] ABSTRACT

Lower polyhydric alcohols are prepared by catalytic hydrogenolysis of sucrose in an aqueous solution by using a catalyst whose active material essentially consists of from 0 to 100% by weight of cobalt,
from 0 to 85% by weight of copper and
from 0 to 80% by weight of manganese, the percentages being based on the content of the metals.

8 Claims, No Drawings

PREPARATION OF LOWER POLYHYDRIC ALCOHOLS

This application is a continuation of application Ser. No. 785,223, filed Oct. 28, 1991, now abandoned, which in turn is a continuation of application Ser. No. 555,663, filed Jul. 18, 1990, now abandoned, which in turn is a continuation of application Ser. No. 385,545 filed May 26, 1989, now abandoned.

The present invention relates to a novel process for the preparation of lower polyhydric alcohols by catalytic hydrogenolysis of sucrose in an aqueous medium.

Polyhydric alcohols, such as ethylene glycol and 1,2-propylene glycol, are essential components of antifreezes and useful starting materials for industrially important esterification and etherification products, of which the polyester of ethylene glycol and terephthalic acid is particularly noteworthy owing to its importance as a fiber raw material.

It is known (G.v. Ling et al., Ind. Eng. Chem. Prod. Res. Develop. 9, 2 [1970], 211) that sucrose, dissolved in a methanol/water mixture, can be cleaved under hydrogenating conditions using a $CuO/CaO_2/SiO_2$ catalyst, the organic mixture obtained from the reaction containing about 31% by weight of glycerol, 16% by weight of ethylene glycol, 18% by weight of 1,2-propylene glycol, 16% by weight of hexitols and 19% by weight of other products.

If ethanol is used as the solvent and copper chromite as the catalyst, according to G. Natta et al. in Chem. Ber. 76 7 [1943] Table 1, page 644, the products are sorbitol and undistillable polyhydric alcohols as well as up to 54% by weight of 1,2-propylene glycol and 14% by weight of glycerol, the percentages being based on the amount of sucrose used.

According to R. Weidenhagen and H. Wegner, Chem. Ber. 71, 12 [1938], 2712 et seq., the formation of glycerol can be completely suppressed in favor of 1,2-propylene glycol if the hydrogenolysis is carried out in two stages. In the first stage, the aqueous sucrose solution is hydrogenated in a neutral medium in the presence of a nickel catalyst activated with molybdenum. The reaction is then stopped and the resulting hydroxyacetone is distilled off. This is then completely hydrogenated in aqueous solution in the presence of the same catalyst, after the addition of calcium hydroxide. 25 g of propylene glycol are obtained from 68.4 g of sucrose in this manner.

It is an object of the present invention to provide a single-stage process for the catalytic hydrogenolysis of sucrose in aqueous solution in which ethylene glycol and 1,2-propylene glycol are obtained as the main components.

We have found that this object is achieved by a process for the catalytic hydrogenolysis of sucrose in aqueous solution, wherein a catalyst is used whose active material essentially consists of
from 0 to 100% by weight of cobalt,
from 0 to 85% by weight of copper and
from 0 to 80% by weight of manganese
the percentages being based on the content of the metals.

According to the definition, the catalyst to be used according to the invention may contain cobalt as the sole metal or may consist of only two metals; however, it has proven advantageous if the catalysts contain all three metals, the manganese content being not less than 5% by weight.

Groups of catalysts which are particularly suitable have the following compositions:
a) from 5 to 90% by weight of Co,
from 5 to 80% by weight of Cu and
from 5 to 75% by weight of Mn
b) from 0 to 5% by weight of Co,
from 25 to 75% by weight of Cu and
from 20 to 75% by weight of Mn
c) from 75 to 97% by weight of Co,
from 0 to 5% by weight of Cu and
from 5 to 20% by weight of Mn.

Preferably used catalysts for the novel process are those which are obtainable by a procedure in which the relevant metals are mixed in the form of aqueous salt solutions and are precipitated together from this mixture by adding a base, the precipitated material is isolated, dried and converted by calcination into a mixed oxide and, if desired, the latter is activated by reduction with hydrogen.

For the preparation of aqueous starting solutions of the relevant metals, their nitrates, sulfates or acetates are advantageously used. Precipitation from the aqueous salt solution is preferably effected by the addition of water-soluble hydroxides or carbonates, alkali metal carbonates, in particular $Na_2CO_3$, being particularly preferred.

The precipitation is particularly advantageously carried out according to DE-C2 23 21 101 by a procedure in which, in a first stage, the aqueous starting solution of the relevant metals is brought to a pH of not less than 8 by means of an alkali metal carbonate solution at from 40° C. to 70° C. and thereafter, in the second stage, precipitation is completed by careful acidification, ie. the introduction of additional aqueous metal salt solution, and a pH of 6.8–7.5 should be maintained.

The precipitated material is usually obtained by filtration and is washed and dried. It is then advantageously calcined at from 420° C. to 550° C. with air.

The catalyst obtained in the calcination is activated by reducing it in a generally known manner at elevated temperatures, advantageously from 200° C. to 600° C., in a stream of hydrogen. This procedure is preferable to activation in situ, ie. gradual activation in the course of the hydrogenolysis.

The catalysts are preferably used as complete catalysts, ie. the entire catalyst consists of the catalytically active material. However, the catalytically active material may also be applied to an inert carrier. Such supported catalysts are prepared, for example, by precipitating the active components from their common aqueous solution in the form of hydroxides or carbonates onto the carrier, drying the product and calcining and activating it in the manner described.

The novel process can be carried out batchwise or continuously. In the continuous procedure, the aqueous sucrose solution and the hydrogen are advantageously passed over a fixed-bed catalyst heated at the reaction temperature. The catalyst bed may consist of various moldings, which are obtainable, for example, by powdering the mixed oxide obtained after the calcination, converting the resulting oxide powder to a paste, for example with an aqueous solution of an inorganic acid capable of forming polyacids, molding the said paste to give extrudates, beads or pellets and then calcining and reducing these in a conventional manner.

In the batchwise procedure, in which, for example, the aqueous sucrose solution and the catalyst are introduced into a pressure vessel and heated to the reaction temperature under a hydrogen atmosphere, the activated catalyst is advantageously used in powder form.

The powder is usually prepared using the wet milling method since the activated catalysts are pyrophoric. A mean particle size of from 0.005 to 0.5 mm (maximum particle diameter) is preferred. Usually, from 30 to 100 g, preferably from 50 to 70 g, of activated powder catalyst are used per kg of a 50% strength by weight aqueous sucrose solution.

In order to obtain catalysts having advantageous mechanical properties, inorganic acids capable of forming polyacids, for example sulfuric acid, boric acid, phosphoric acid, molybdic acid, tungstic acid and/or their salts, such as trisodium phosphate, sodium tetraborate, potassium dihydrogen phosphate, calcium hydrogen phosphate, magnesium hydrogen borate, aluminum phosphate, sodium molybdate, ammonium molybdate, ammonium vanadate and sodium tungstate, are advantageously added to the aqueous starting solution.

In another possible method of introducing these additives, the calcined material is impregnated with an aqueous solution of the corresponding salt of the inorganic acid and then treated with a mineral acid, eg. nitric acid. The product is then dried, reduced in a stream of hydrogen in the manner described and wet-milled. The amount of inorganic acid and/or its salts is in general from 0.1 to 15% by weight, based on the reduced form of the catalyst. Such catalysts containing additives have, for example, less tendency to agglomerate when used as catalyst powder with thorough stirring.

In order to increase the effective surface area and hence the activity of the catalytically active components, poorly reducible oxides, such as MgO, CaO or $Al_2O_3$, can be added as further additives prior to calcination, the amount of the said oxides being not more than 50% by weight, based on the activated form of the catalyst. However, by means of this increase in activity, the selectivity of the cleavage under hydrogenating conditions may be reduced with respect to the desired lower alcohols, so that it is preferable for these additives to be omitted or to be used in only small amounts, for example not more than 10% by weight.

We have also found that the selectivity depends on the reaction temperature. Particularly high yields of ethylene glycol and 1,2-propylene glycol are obtained at from 220° C. to 280° C., in particular from 240° C. to 270° C.

At higher temperatures, further hydrogenolysis increasingly takes place, giving monohydric alcohols, such as ethanol, isopropanol, butan-2-ol or various hexanols. Hydrocarbons, such as methane, are then also formed in some cases. At lower temperatures, in addition to sorbitol, mannitol and hexane-1,2,6-triol, greater amounts of, in particular, hexane-1,2,5,6-tetrol are obtained as byproducts.

Hexane-1,2,5,6-tetrol is a useful starting compound for all polyurethane chemistry. At reaction temperatures of from 200° C. to 240° C., in particular from 220° C. to 230° C., its content may be up to 25% by weight, based on the total amount of the organic components in the reacted mixture.

The selectivity of the novel process depends on the hydrogen pressure as follows. Under pressures below 250 bar, selectivity decreases sharply with increasing formation of hexitols, and above 700 bar the tendency to further hydrolysis with formation of monohydric alcohols and hydrocarbons increases. Particularly in the range from 300 to 700 bar, the selectivity is virtually independent of pressure. The range from 250 to 350 bar is preferred in practice.

The concentration of the aqueous sucrose solution has only little effect on the product distribution. Only at concentrations above 70% by weight of sucrose does the selectivity of the novel process decrease substantially. Concentrations of from 30 to 60% by weight are preferred.

It is also advantageous to ensure thorough mixing of the reactants, as can be achieved, for example, by using a high speed turbine stirrer when carrying out the reaction in a pressure vessel. The course of the reaction can be monitored from the hydrogen pressure. When only a small amount of hydrogen is absorbed, the reaction is at an end. This point is usually reached after a few hours.

Under the stated preferred conditions, as a rule the following yields are obtained, based on the total amount of the organic components in the reacted mixture:

| | |
|---|---|
| 1,2-propylene glycol | 50–65% by weight, |
| ethylene glycol | 20–25% by weight, |
| 1,2-butylene glycol | 5–7% by weight and |
| hexane-1,2,5,6-tetrol | 3–10% by weight |
| glycerol | <1% by weight. |

The reactions go to completion, ie. sucrose is no longer detectable.

EXAMPLE a) Preparation of the Catalyst

The pH of an acidic starting solution of 23.78 kg of cobalt(II) nitrate hexahydrate, 4.65 kg of copper(II) nitrate hexahydrate, 1.83 kg of manganese(II) nitrate hexahydrate and 0.20 kg of a 75.3% strength by weight aqueous phosphoric acid in 17.5 kg of water was initially brought to 8.5 by stirring into it a 20% strength by weight aqueous sodium carbonate solution, and then reduced to 7 by introducing additional starting solution. The resulting precipitate was filtered off, washed, dried, and calcined at 500° C. with air. Thereafter, 4 kg of the calcined material were powdered and mixed with 626 g of a solution of 166 g of molybdenum trioxide in 460 g of 20% strength by weight ammonia and with 1.58 kg of an 11.7% strength by weight nitric acid.

The material obtained was extruded and dried and the extrudates were calcined in a conventional manner, reduced and then wet-milled to give a powder having a mean particle size of 0.1 mm. In the unreduced form, the catalyst had the following composition:

| | |
|---|---|
| 66.8% by weight of CoO | (=72% by weight of Co)* |
| 19.2% by weight of CuO | (=21% by weight of Cu)* |
| 7.1% by weight of $Mn_3O_4$ | ( =7% by weight of Mn)* |
| 3.4% by weight of $H_3PO_4$ and | |
| 3.5% by weight of $MoO_3$ | |

*based on Co + Cu + Mn = 100%.

b) Catalytic Hydrogenolysis Procedure

In a pressure vessel having a capacity of 250 ml, 11.5 g of the finely divided, activated catalyst a) were suspended in 140 g of a 50% strength by weight aqueous sucrose solution.

The pressure was then brought to 180 bar with hydrogen and the mixture was heated to the reaction temperature of 250° C. in the course of 15 minutes while stirring thoroughly. When 180° C. had been reached, the beginning of the reaction was indicated by intensive absorption of gas. The drop in hydrogen pressure accompanying this gas absorption was immediately compensated, and the pressure was kept at from 280 to 300 bar in the further course of the reaction in a corresponding manner.

The reactions slow down after 30 minutes and, after a total reaction time of 4.5 hours, the reaction was terminated by cooling and letting down the pressure vessel. The catalyst was filtered off from the reacted mixture, which was analyzed by HPLC and GC. In addition, the water content was determined by the Karl Fischer method.

The analysis gave 59% by weight of $H_2O$ and 41% by weight of organic components.

The following organic components were determined:
60% by weight of 1,2-propylene glycol,
20% by weight of ethylene glycol,
7% by weight of 1,2-butylene glycol,
5% by weight of hexane-1,2,5,6-tetrol,
1% by weight of hexane-1,2,6-triol,
4% by weight of monohydric alcohols, such as ethanol, n-propanol and 2-butanol, and
3% by weight of unidentified compounds.

We claim:

1. In a process for the preparation of a lower polyhydric alcohol by catalytic hydrogenolysis of sucrose in an aqueous medium, at elevated temperatures and pressures, the improvement for selectively producing ethylene glycol and 1,2-propylene glycol which comprises:

using a catalyst in which the active material consists essentially of a reduced mixture of the oxides of the metals cobalt, copper and manganese, containing at least 5 up to not more than 80% by weight of manganese and up to not more than 85% by weight of copper, the percentages being based upon a total content of said metals of 100%, said catalyst being prepared by mixing the relevant metals in the form of their aqueous salt solutions and precipitating them together from this mixture by adding a base, then isolating and drying the precipitated material and converting the dried precipitate by calcination into a mixed oxide which is subsequently activated by reduction with hydrogen at an elevated temperature of at least about 200° C.; and carrying out the hydrogenation reaction at a temperature of from 220° C. to 280° C. and at a hydrogen pressure of from 250 to 700 bar.

2. A process as claimed in claim 1, wherein the catalyst used is prepared by precipitating the salts of said metals with a water-soluble hydroxide or carbonate as the base, and subsequently converting the precipitate by calcination with air at 420° C. to 550° C. into a mixed oxide which is then activated by reduction with hydrogen at a temperature of from 200° C. to 600° C.

3. A process as claimed in claim 1, wherein the catalyst contains as the active metal component:
from 5 to 90% by weight of cobalt;
from 5 to 80% by weight of copper; and
from 5 to 75% by weight of manganese.

4. A process as claimed in claim 1, carried out at a temperature of from 240° C. to 270° C.

5. A process as claimed in claim 1, carried out at a pressure of from 250 to 350 bar.

6. A process as claimed in claim 1, wherein the concentration of the sucrose in said aqueous medium is up to 70% by weight.

7. A process as claimed in claim 1, wherein the concentration of the sucrose in said aqueous medium is from about 30 to 60% by weight.

8. A process as claimed in claim 2, wherein the catalytic hydrogenolysis is carried out on an aqueous sucrose solution having a sucrose content of up to 70% by weight, at a temperature of 240° C. to 270° C., and at a pressure of from 250 to 350 bar.

* * * * *